United States Patent [19]
Wortrich et al.

[11] Patent Number: 5,897,524
[45] Date of Patent: Apr. 27, 1999

[54] COMPACT CASSETTE FOR OPHTHALMIC SURGERY

[76] Inventors: Theodore S. Wortrich, 2535 E. First St., Long Beach, Calif. 90803; Charles Beuchat, No. 6 Westport, Irvine, Calif. 92620

[21] Appl. No.: 08/823,433

[22] Filed: Mar. 24, 1997

[51] Int. Cl.⁶ .................................................. A61M 1/00
[52] U.S. Cl. .............................................................. 604/30
[58] Field of Search ................................ 604/65–67, 30, 604/31, 246–249, 49–53; 128/DIG. 12, DIG. 13

[56] References Cited

U.S. PATENT DOCUMENTS

| | | |
|---|---|---|
| 4,493,695 | 1/1985 | Cook . |
| 4,713,051 | 12/1987 | Steppe et al. . |
| 5,041,096 | 8/1991 | Beuchat et al. . |
| 5,125,891 | 6/1992 | Hossain et al. ........................... 604/34 |
| 5,163,900 | 11/1992 | Wortrich . |
| 5,267,956 | 12/1993 | Beuchat . |
| 5,282,787 | 2/1994 | Wortrich . |
| 5,364,342 | 11/1994 | Beuchat et al. . |

*Primary Examiner*—John D. Yasko
*Assistant Examiner*—Manuel Mendoz
*Attorney, Agent, or Firm*—Merchant & Gould

[57] ABSTRACT

A cassette configuration, operative parts of which may be disposable or resterilizable, is configured with an adapter that may be mounted within the cassette receiving portal of a console that uses a peristaltic pump spaced apart from actuator and vent controls to engage the lower end wall of a cassette. The adapter is asymmetrically mounted in the available space, and allows a tubing loop from one side of a cassette inserted under it to be threaded through the peristaltic pump and to be seated in a bore in the adapter on the opposite side. A lower edge of the cassette fits into an interface slot in the console, and the interior tubing configuration enables clamping of irrigation and vent lines, while providing aspiration and irrigation flows to and from a handpiece. Within the cassette or in the console, flow control elements are provided to enable alternative venting of either air or fluid into the aspiration system to prevent excessive suction at the operative site. At the same time, the flow system and the pressure sensing and venting arrangement are configured to allow resterilization of the cassette if desired.

13 Claims, 7 Drawing Sheets

COMPACT CASSETTE FOR OPHTHALMIC SURGERY

FIELD OF THE INVENTION

This invention relates to cassettes for controlling fluid flows during surgical procedures, and more particularly to cassettes, which may be disposable or reusable, for use in ophthalmic surgery systems having peristaltic pumps rotating in a plane parallel to and above actuator and venting controls, and to arrangements for allowing suction levels to be released by different optionally usable devices.

BACKGROUND OF THE INVENTION

Early in the development of fluid control systems for surgical procedures, the practice was to use sets of flexible tubing lengths that were threaded through different positions in a console to control the flow of irrigation fluid to a surgical site, as well as the flow of aspirated matter from the site. The console included displaceable or fixed clamps and variable pumps to control flow paths and flow rates. In ophthalmic surgery, for example, the irrigation and aspiration lines were coupled to a handpiece, often having an ultrasonically vibrated tip, used by the surgeon for incision and for extraction of matter. Irrigation fluid passed through one or more orifices in the handpiece tip and aspirated fluid was withdrawn through other orifices in the tip.

Originally, the tubing lines would be manually threaded past actuator clamp positions, and the aspiration line would feed to a peristaltic pump or suction source. The next logical design improvement was to arrange the control console so as to incorporate clamps and suction sources in geometries such that they could be accessed by flexible tubing within an enclosure or cassette. In one type of cassette, as shown by Cook U.S. Pat. No. 4,627,833, the cassette housing included back-up surfaces against which flexible tubing could be pinched down to closure through an opening in the side of the cassette by an external actuator, while suction was drawn by an external source through a collection vessel, so as to cause the aspirated fluid to flow into the collection vessel. In another example, evidenced by Steppe et al., U.S. Pat. No. 4,713,051, this approach was modified to provide a cassette with a sidewall which was configured with a series of clamp openings and a separate concave back-up surface for tubing to be engaged by a peristaltic pump. Both of these systems incorporated accessible apertures for fluid vents, although Cook vented air and Steppe vented liquid. The vent apertures were used to cooperate with pressure sensing or pressure relief units in the console, enabling the system or surgeon to relieve pressure and prevent damage to sensitive eye tissues.

These cassettes were primarily intended to be disposable, because blood or blood-containing matter in tubing creates an unacceptable possibility of cross-contamination, unless effective sterilization procedures are used. Adequately safe sterilization procedures often are not regarded as sufficiently cost effective in this country. Nonetheless, under some circumstances and in some countries, sterilization of cassettes and repeated reuse are preferred.

It has also been recognized that the functions of the tubing in a cassette are separable and that only certain parts of the tubing need be disposable or resterilizable. Thus, the relative convenience of single-step insertion of a unitary cassette may provide no real advantage over a unit requiring more than one step, if the additional steps are inherently easy to perform. This benefit is exemplified by Wortrich U.S. Pat. No. 5,163,900, in which the configuration of the receptacle for the cassette is modified by a non-disposable adapter. The adapter is configured so as to allow simplification and substantial cost reduction of the disposable cassette that fits in it. The benefits are also illustrated by Wortrich U.S. Pat. No. 5,282,785, in which the disposable cassette is also substantially reduced in cost and size while the adapter section forms a convenient handling and loading tray. Placement of the aspiration tubing relative to a peristaltic pump is facilitated by a surface guide groove in the adapter.

These approaches demonstrate that by awareness of practical conditions at the operative site and by internal separation of functions, significant cost advantages can be realized for different systems with no meaningful penalty in convenience.

There is yet another type of console using fluid flow control for ophthalmic surgery applications. The system and the related cassette are shown in Beuchat et al. U.S. Pat. No. 5,267,956, the commercial version being that depicted in FIG. 27 in that patent. In this Beuchat et al. system, the cassette is configured with a flat distal face having an outline that fits within a portal in the console. The front face of the mounting portal terminates at a bottom interface slot through which upwardly directed actuator clamps extend, when desired, to close off passageways in a cassette mounted in the portal. A system-coupled sensing aperture is disposed between the two clamps to enable communication between the cassette interior and a vacuum sensor in the console. To allow the pressure level to be communicated from the cassette interior to the console without the danger of fluid return into the cassette, a largely hydrophobic filter is included in the conduit in the cassette. To prevent locking up the control system while limiting reverse flow, the filter includes a small hydrophobic area and is thus known as a "spotted hydrophobic filter". The top of the cassette includes a loop of flexible tubing that seats around the periphery of a peristaltic pump in the upper portion of the portal.

The Beuchat et al. cassette has integrally molded internal passageways and uses an elastomeric insert along its bottom surface that stretches under clamp action to close off passageways. The cassette can be conveniently mounted in place, but has a number of limitations. The intricate internal and integrally molded passageways are difficult to sterilize thoroughly, so that reuse is usually not feasible. The integrally molded passageways are also not capable of accommodating pressure differences by expansion or contraction, so that an interior "capacitance chamber" must be provided to allow for pressure differences. The interior spotted hydrophobic filter, once used, cannot be cleaned of contaminants, so that the cassette itself cannot be reused.

The rigid internal passageways and the complex internal configuration mean that this type of cassette is not suitable for reuse in those countries which widely practice resterilization because of preference or economic necessity. In addition to the complex internal flow passageways, resterilization is precluded by the presence of the hydrophobic filter that is used in the pressure sensing line to the console. It is obviously desirable to utilize the same basic cassette for disposable and resterilizable modes, if these limitations can be overcome.

Another option which is often desired by users of these cassettes is the ability to chose either air venting or fluid venting for suction release of the aspiration line. In ophthalmic systems, means have been provided for many years to counteract the danger of excessive suction being applied through the aspiration line into the eye. A technique developed at an early stage in the use of ophthalmic surgery kits was to provide a coupling line, normally closed by a clamp, between the aspiration line and the source of irrigation fluid. When it was required to relieve the suction pressure quickly, relief of the clamp released irrigation fluid into the aspiration line, breaking the suction and avoiding the danger.

Some users, however, prefer to break the suction by venting to air, which is less instantaneous, because of the compressibility of air and the flexibility of the lines. Surgeons vary in their preferences as to the type of venting to be used, and the preferred mode can vary with the stage of the surgical procedure. Whereas liquid venting forces cortical material away with an abrupt flow, the action of air venting is gentler and at lower acceleration. It is evident that a cassette or system which can provide a capability for use of either one of these venting modes, including the option of switching between them, would provide not only substantial cost savings, but also useful operative advantages. Some might prefer to incorporate a vent selection option in the console rather than a cassette. If this can be done, normal operation and use of the cassette should not be affected.

SUMMARY OF THE INVENTION

A compact cassette in accordance with the invention for use with a front portal type of receptacle having an upper peristaltic pump and a bottom interface slot with clamp and vent connections comprises a two-piece assembly, including an upper bracket that mounts detachably in the portal. The upper bracket receives a small cassette having interior flexible tubing turned about back-up posts adjacent access openings in the bottom wall which align with the clamp actuators in the interface slot of the console. A sensing opening between the access openings couples to the interior tubing within the cassette, and a spotted hydrophobic filter may optionally be fixed or removable in the coupling to the aspiration line. The aspiration tubing extends outwardly from an upper corner of the cassette, providing a tubing loop for wrapping about the peristaltic pump after the cassette is inserted. The tubing loop includes an end coupler seating within a retainer in the bracket, and a tubing end for waste matter extending from the coupler can be inserted in a collection bag proximate to the front of the cassette. Thus, the cassette may be inserted into the pre-installed bracket, above the interface slot, the extending aspiration tubing length can be wrapped about the peristaltic pump as the coupler end is seated in its retainer, and the free tubing end can be placed in the waste collection bag, all in a simple and quickly effected sequence.

A feature of the invention is that the upper bracket for mounting in the console portal receives the top of the cassette and engages the distal broad face of the cassette while providing means for holding the exterior pump loop and waste output extension in position. The cassette has a top extension between and above side shoulders. The pump loop extends from a side shoulder that is offset relative to the bracket, to the other shoulder, which fits into and below the corner shoulder of the bracket, assuring both vertical and lateral positioning. Consequently, the cassette is asymmetrically positioned relative to the upper part of the bracket, but firmly secured. Another feature is that the retainer in the bracket shoulder registers with the coupler at the pump loop in such manner that the coupler slides in readily but will not release without positive action.

It is important to note that the flow conduits inside the cassette are flexible, so that pressure differences are automatically accounted for to some degree by wall expansion and compression. The same housing can be used whether a filter is to be incorporated or not, and internal assembly requires attachment of only a few fittings at Tees within the cassette.

The compact cassette thus comprises a small inexpensive unit, with short lengths of interior flexible tubing. The broad proximal face includes an opening through which the spotted hydrophobic filter may be disengaged from its fittings, so that the entire unit may be resterilized, and a new filter inserted thereafter. In all circumstances, the wrapping of the pump loop around the peristaltic pump is simple, virtually instantaneous, and follows an obvious path.

Suction release can be an important consideration for various surgical procedures, and since different types are preferred for different practical situations, cassettes in accordance with the invention can be used to provide optional air or liquid venting in different ways. By incorporating an occludable mechanism with a vent line in the console that is coupled to the sensing conduit, an operator or surgeon may select, at the console, venting by liquid from the cassette or venting by air within the console. For control of venting options at the cassette, the cassette may include a multi-position valve element disposed in the vent line that is coupled to the aspiration line. The valve element receives input both from an air line, through a unidirectional element, and from the irrigation line. Whether fluid or air is used to vent is controlled by changing the position of the control valve, an end of which can be accessible from the outside of the cassette. Consequently, the mode of use (air or fluid venting) can be determined during manufacture of the product, or at the surgical site, if desired.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
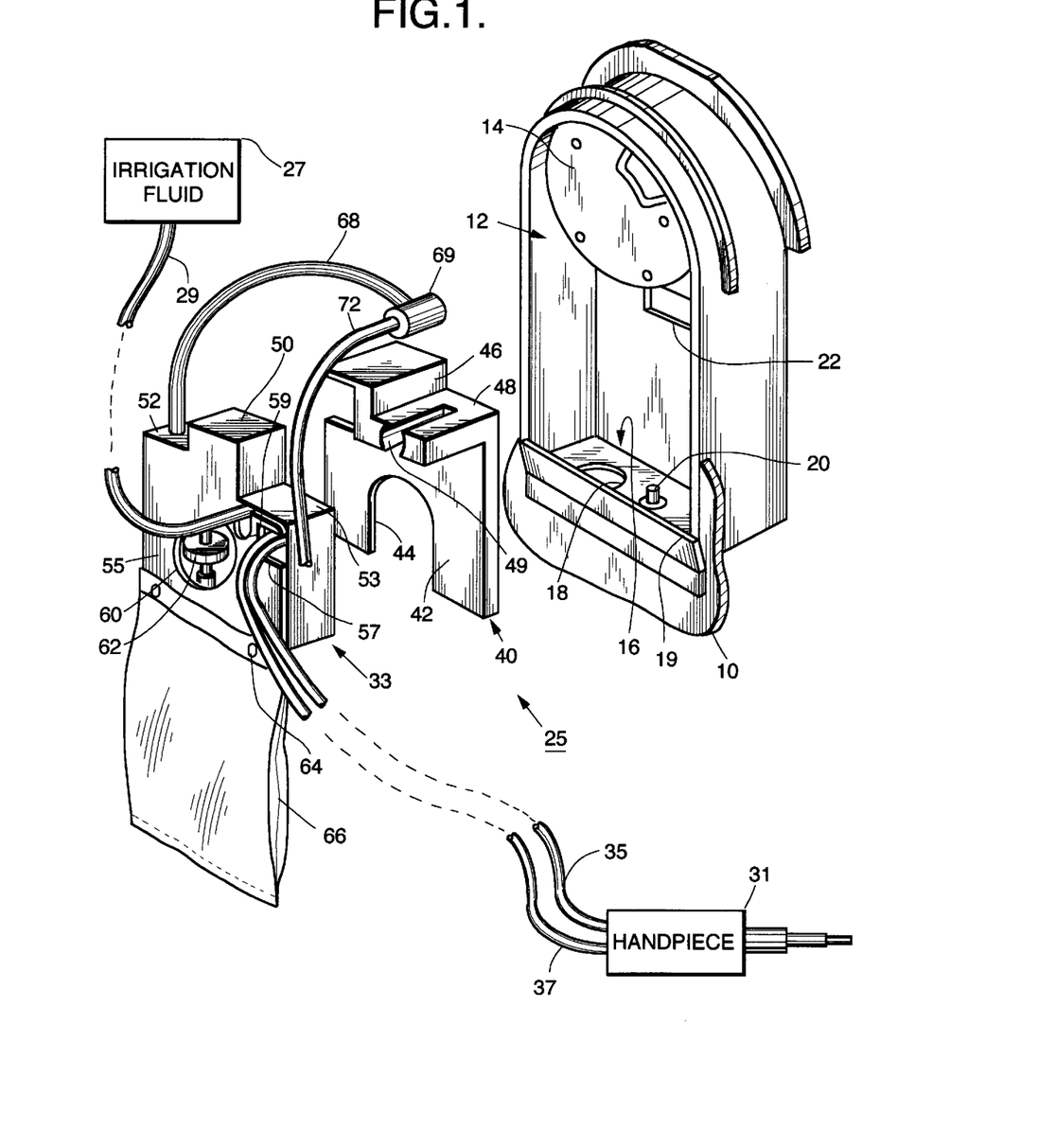
FIG. 1 is an exploded view of a compact cassette in relation to the console portal in which it is to be mounted, the cassette being coupled to a handpiece and comprising both an adapter bracket and a cassette housing.
Figure 2:
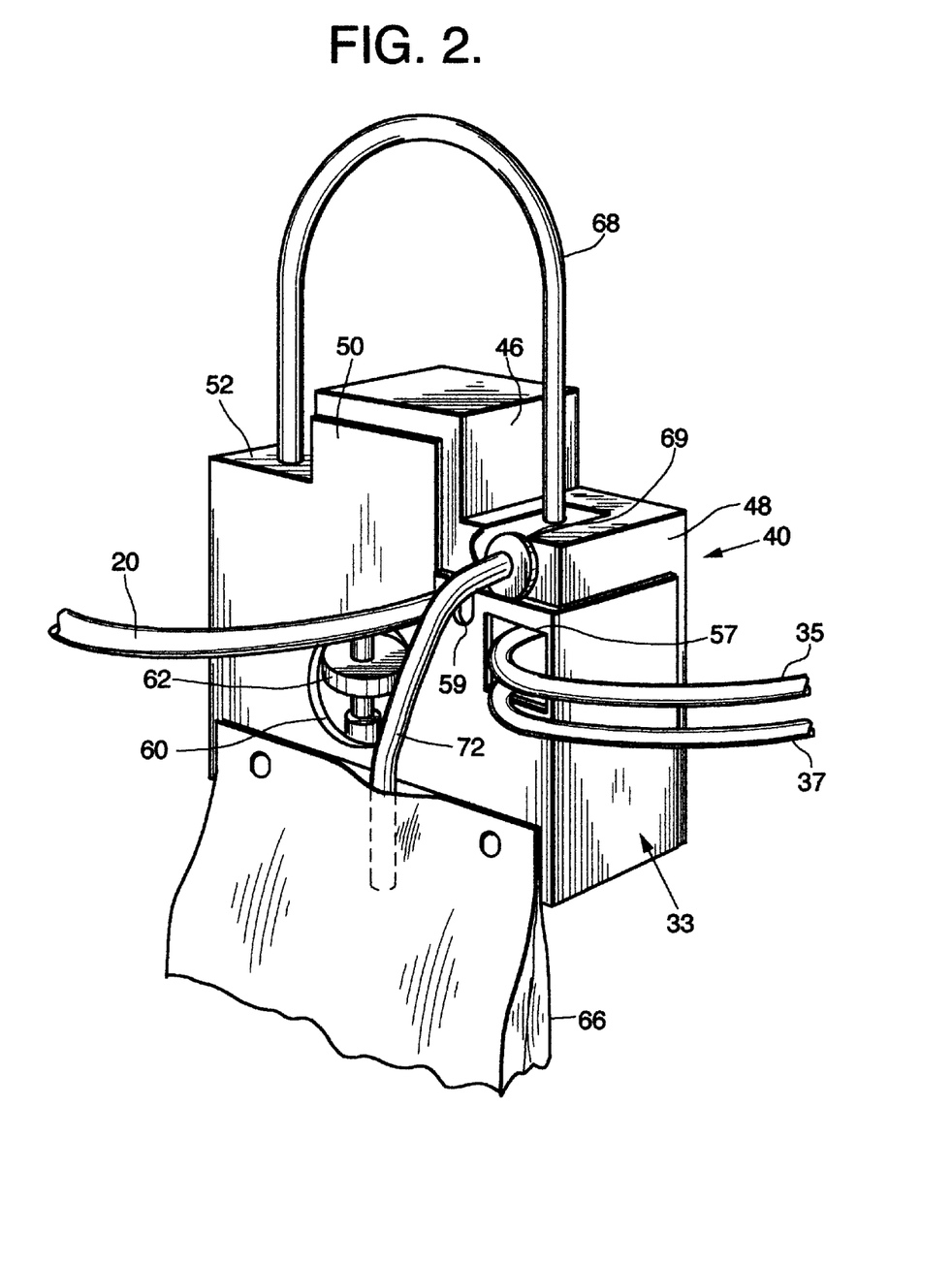
FIG. 2 is a perspective partial view of the cassette and adapter bracket of FIG. 1 when assembled.

A cassette in accordance with the invention, referring now to FIGS. 1 and 2, is for operation with a console 10, only a fragment of the front panel of which is shown, of the type having a cassette portal 12 in the form of a recessed archway with a greater height than depth dimension, for receiving the cassette in a substantially upstanding position. In the upper region of the cassette portal 12, a peristaltic pump 14 is disposed below the curved top, which itself forms a backup surface for the peristaltic pump rollers, in known fashion. At the bottom of the portal 12 is an interface slot 16 having openings for spaced apart actuator elements 18, 19 disposed for vertical operation upwardly toward the cassette, in known fashion. Between the separate actuators 18, 19 is a sensing port 20 for communicating suction level variations into the interior of the console 10 for the vacuum sensing function used in this type of system.

On the distal face of the cassette portal 12 is a latch opening 22 for engaging a catch, pilot pin or similar element in the cassette that is to be inserted.

A cassette assembly 25 in accordance with the invention is configured in two principal parts, as described below, and functions in association not only with the console but with an irrigation fluid source 27 which provides sterile fluid in a line 29 to the cassette. The cassette assembly 25 also functions with a handpiece 31 in the surgical field that is usually spaced a distance from the cassette body 33 at the console 10. An aspiration line 35 from the handpiece to the cassette and an irrigation line 37 to the handpiece from the cassette are relevant to the present description. Controls at the handpiece 31 for flow, lines for electrical energization of ultrasonic vibration, and other features may be used but are not depicted here.

The cassette assembly 25 includes an adapter bracket 40, which is in part asymmetrically configured relative to the cassette portal 12 and to the cassette body 33. The adapter bracket 40 includes a planar vertical plate 42 at its distal side, with conventional means for engaging the latch opening 22 in the cassette portal 12. The plate includes an arch opening 44 which provides clearance for the perimeter of a spotted hydrophobic filter. A proximally extending L-shaped top portion 46 of the adapter bracket 40 fits below the peristaltic pump 14 when the adapter bracket 40 is inserted in the cassette portal 12. The top portion 46 extends laterally to an adjacent shoulder 48 which is at the right hand side (as viewed in FIGS. 1 and 2) of the adapter bracket 40. The shoulder 48 includes a horizontal bore 49 extending to a given depth, related to the length of the fitting it is to receive, so as to provide an end stop surface. The vertical dimension of the shoulder 48 is slightly less than the diameter of a cylindrical fitting or coupler to be placed within it, so that the cylindrical element can be digitally gripped both above and below for easy insertion and removal. The shape of the bore and coupler need not be complementary, since only smooth insertion and adequately secure retention are needed, after the pump loop is formed. A differently shaped fitting and a clip retainer will suffice, but the cylindrical bore and mating fitting provide good visual guidance and convenient placement and removal.

The cassette 33 is typically of an engineering plastic suitable for sterilization and has an approximately centrally positioned head block 50 protruding above its upper edge, for fitting within and below the L-shaped top 46 of the adapter bracket 40. The head block 50 is integral with the remainder of the cassette housing, and separates a tube loop shoulder 52 on one side (here viewed as the left) from a slightly lower shoulder 53 on the other (right) side. The latter shoulder 53 is closed and fits under the shoulder 48 on the adapter bracket 40 when the units of the cassette assembly 25 are placed together. This assures both vertical and lateral placement, when the bottom of the cassette is in the interface slot of the console.

The proximal face 55 of the cassette 33 has openings for various elements, such as an opening 57 for the lines to the handpiece 31, and an opening 59 for the irrigation input, both of these openings being substantially immediately below the right shoulder 53. In the central lower region of the proximal face 55, an opening 60 is provided as clearance for the periphery of an interior spotted hydrophobic filter 62. If the hydrophobic filter 62 is to be replaceable, this opening 60 is large enough, and suitably shaped, to allow extraction and reinsertion of the filter therethrough. Along the lower edge of the proximal face 55 are a pair of grommets 64 for retaining a waste collection bag 66. The grommets 64 or other fasteners allow replacement of the waste collection bag 66, which is necessary if the cassette is to be reused. However, the waste pumped out can be directed into a separate proximate container or location, and no bag need be attached to the cassette.

At the left or tube loop shoulder 52 of the cassette 33, a length of pump loop tubing 68 extends outwardly to a cylindrical coupling 69 sized to fit smoothly, without friction, into the horizontal bore 49 in the adapter bracket 40. An end length 72 of tubing extending from the end of the cylindrical coupling 69 is insertable into the waste collection bag 66 when the unit is assembled.

Figure 3:
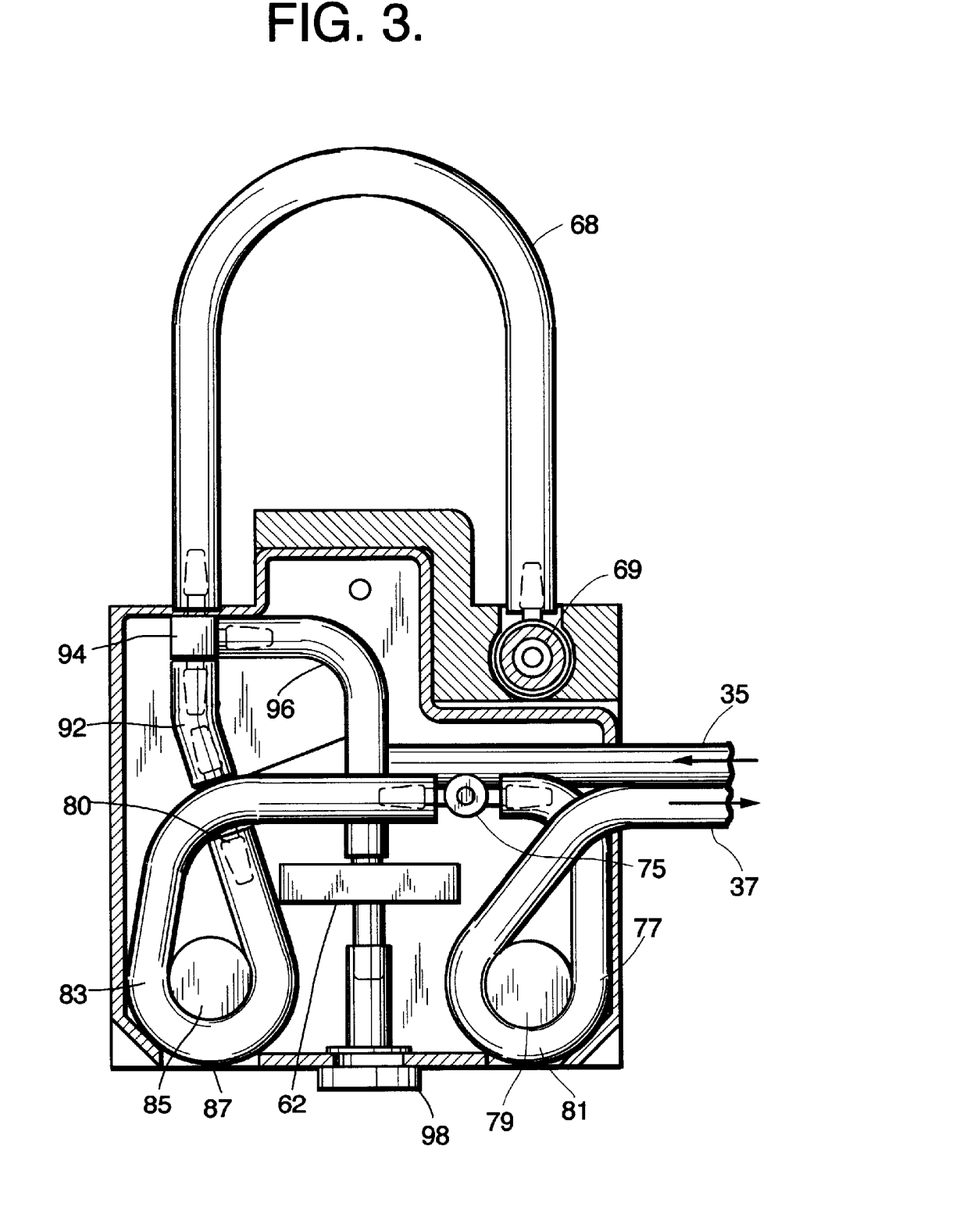
FIG. 3 is a plan view, with side wall removed, of the cassette of FIGS. 1 and 2, showing the conduit disposition therein.

The internal arrangement of tubing within the cassette 33 is depicted in the sectional view of FIG. 3, in which the interior tubing and couplings are shown with one side wall of the cassette removed. The irrigation line 29 feeding in irrigation fluid, and the end length 70 that leads to the waste collection bag from the coupler 69, are not included in this view, because they are perpendicular to the plane of the side wall, projecting into the Figure. The irrigation line input couples to an outwardly directed port of a first Tee 75, where it directed into opposite going flow paths at other branches of the Tee 75. In a first of these flow paths a flexible irrigation tubing 77 wraps around a stop or boss 79 adjacent an irrigation actuator window 81 through which the actuator from the console may act, to pinch the line 77 against the boss 79, terminating irrigation fluid flow out to the irrigation line 37 to the handpiece. The other branch of the first Tee 75 is coupled to a vent flexible tubing 83 which is wrapped around a vent control boss 85 adjacent a vent actuator window 87 through which an actuator in the console may hold the line 83 closed, except when venting is desired. The vent flexible tubing 83 leads to one part of a second Tee 90, a second port of which receives the end of the aspiration line 35 from the handpiece. Thus, with the vent tubing 83 normally closed, the aspiration flow in the aspiration line 35 normally goes out a short coupling tube 92 through a third Tee 94, via aligned ports leading to the pump loop tubing 68 and the cylindrical coupling 69. A third port of the third Tee 94 is connected via a shunt tubing 96 to the hydrophobic filter 62, which is connected directly in line to a sensor fitting 98 in the side wall of the cassette 33, between the actuator windows 81 and 87. The sensor fitting 98 engages the sensing port 20 (FIGS. 1 and 2) in the console and enables a pressure measurement to be made such that pressure regulation can be used, in known fashion, during the surgical procedure.

This internal arrangement of Tees, tubing, vent and filter follows patterns used in prior systems and therefore need be discussed only briefly. Irrigation fluid usually is unclamped and passes out to the irrigation tubing line 37, with flow being returned via the aspiration line 35 from the handpiece, and flowing through the second and third Tees 90, 94, respectively, into the pump loop 68. There the pump loop 68 is engaged by the peristaltic pump, which creates the suction for withdrawing matter from the handpiece and feeding it out through the cylindrical coupling 69 and into the waste collection bag 66 of FIGS. 1 and 2 via the end length 70. Pressure in the aspiration system is constantly monitored by the console, via the sensor fitting 98 and the intercoupling shunt tubing 96, with the hydrophobic filter 62 blocking contamination in the direction from the console to the interior of the cassette. When the surgeon or other operator desires, as when there is an apparent danger of excessive suction in the eye chamber that would cause a collapse, aspiration pressure is substantially immediately relieved by opening the vent flexible tubing 83 at the vent control boss 85, flooding the pump loop tubing 68 as well as allowing some flow into the aspiration line 35, for pressure relief.

The configuration of the cassette assembly 25, as shown in FIGS. 1–3, is unique both in economic and operative terms. When intended to be used as a disposable, only the small and inexpensive cassette 33 with necessary internal tubing and fittings, together with the pump loop tubing 68 and the coupling 69, are involved. The internal lines are short and direct and introduce little impedance to flow. Being flexible, they expand or contract to take up some of the changes in pressure, so that no capacitance chamber or equalizing structure need be utilized.

To install the cassette assembly 25, the asymmetric adapter bracket 40 is first fixed in the cassette portal 12 below the peristaltic pump 14 and above the interface slot 16, engaging the latch opening 22. The adapter bracket 40 can be treated as an essentially permanent unit, although it can be changed after a specified number of uses if the operator desires. To engage the cassette 33 in operative position, it is simply inserted so that the head block 50 fits under the L-shaped top 46, with the right shoulder 53 of the cassette engaging below the corresponding shoulder 48 of the adapter bracket 40. As this is done, the pump loop tubing 68, cylindrical coupling 69 and the end length 70 can be held in the same hand, so that after the cassette body 33 is engaged in position, the pump loop tubing 68 is simply wrapped about the peristaltic pump 14 of FIGS. 1 and 2. The pump loop length is chosen to be such that, when engaged about the pump 14, it is under some tension. The coupling 69 is fed into the horizontal bore 49 in the shoulder 48, and the end length 70 is slipped into the top of the waste collection bag 66, which has been placed on the grommets 64. Because both the top and the bottom of the cylindrical coupling 69 are accessible through the openings in the upper and lower parts of the bore 49, the coupling 69 can easily be inserted but, once inserted, is retained in position.

This arrangement thus enables an inexpensive disposable cassette having a conventional interior coupling arrangement to operate in a different geometry for cassettes than has previously been employed. At the same time, the cassette can be resterilized, if desired. The hydrophobic filter must be changed since such a filter, once used, contains contaminants which cannot be cleaned out or removed. This feature, as well as the incorporation of an alternate venting function, is depicted in the modified cassette of FIGS. 4–6, to which reference is now made.

Figure 4:
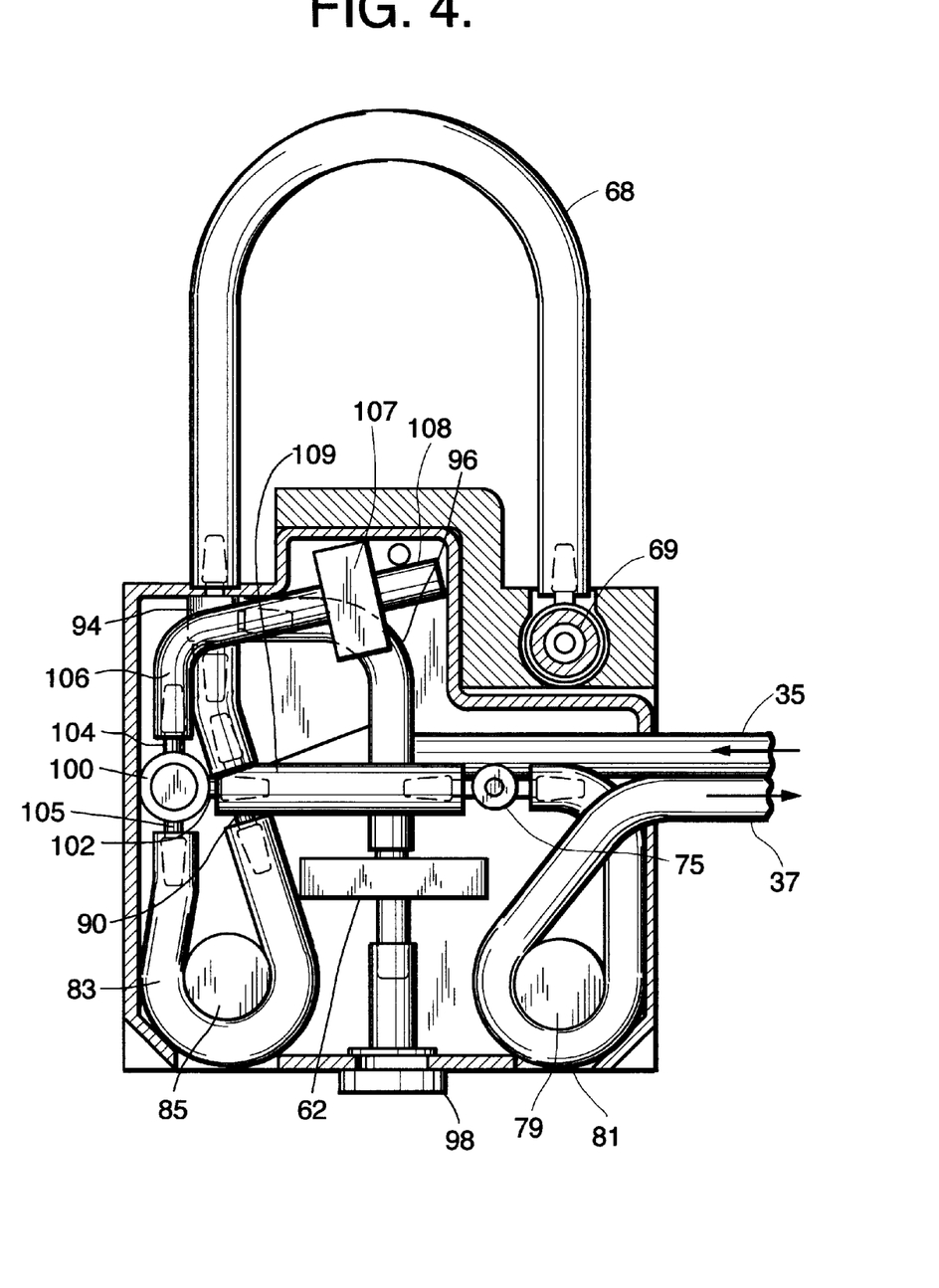
FIG. 4 is a plan view, with side wall removed, of a cassette having the alternative venting feature.
Figure 5:
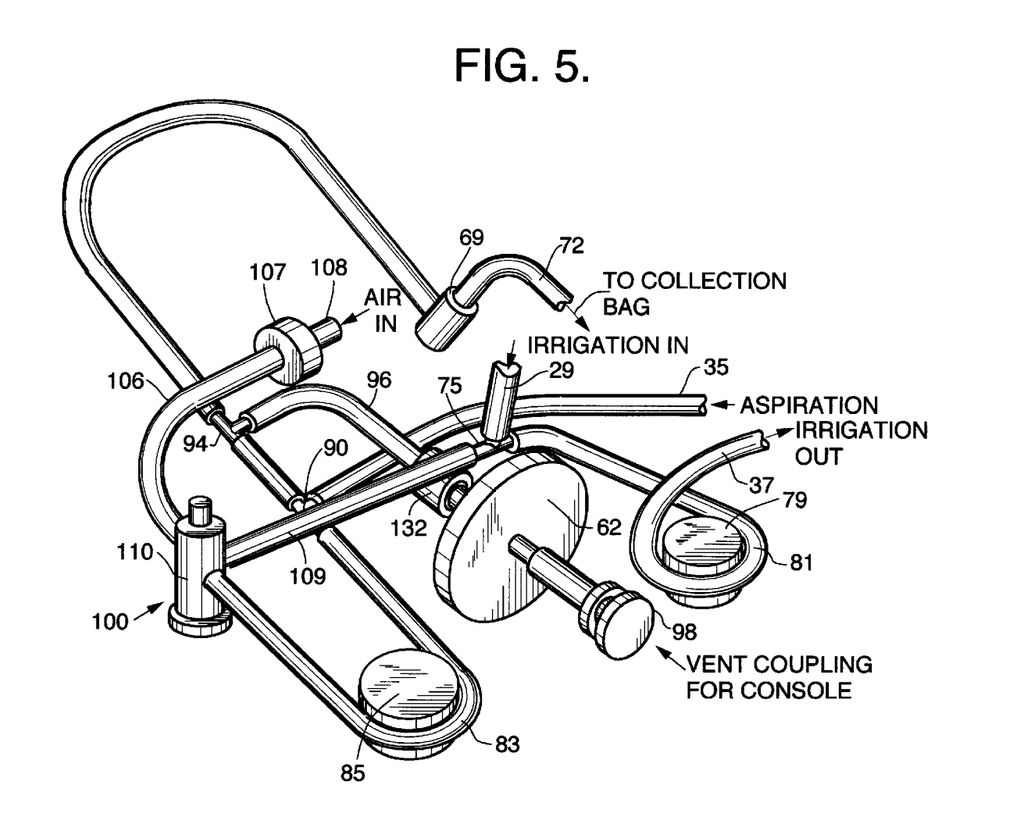
FIG. 5 is a perspective fragmentary view of the conduit arrangement in the cassette of FIG. 4, showing further details thereof.
Figure 6:
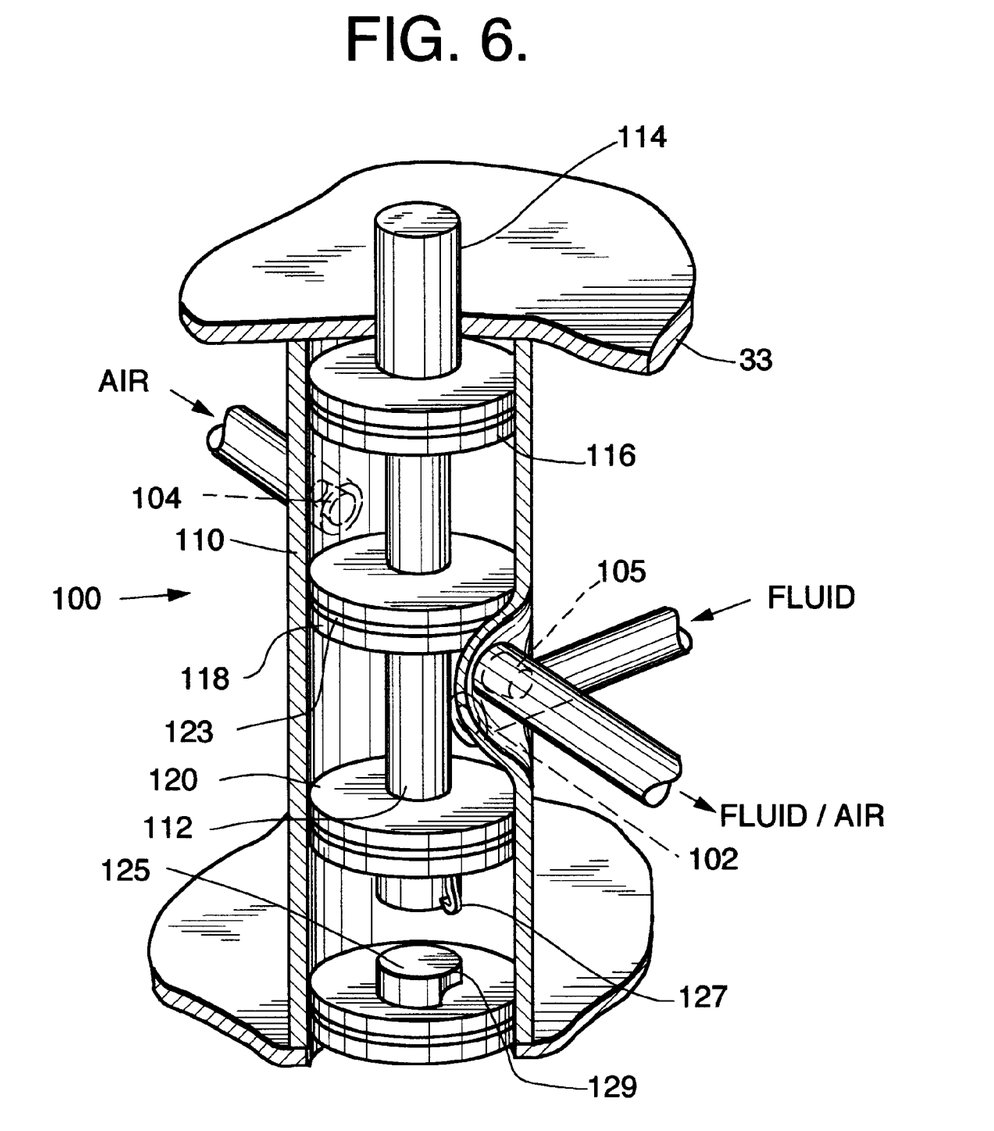
FIG. 6 is a perspective view, partially broken away, of a fragment of the system of FIGS. 4 and 5, showing details of the flow control valve.

As indicated, the vent and irrigation flow controls of FIGS. 4 to 6 have some of the basic structure of the cassette of FIG. 3, but the vent system includes an added coupling in the form of a three port control valve 100 with an input port 102 for the fluid vent, an input port 104 for the air vent line and an output port 105 that couples to the vent flexible tubing 83 section leading ultimately to the third Tee 94. An air vent line 106 coupled to the air input port 104 leads to a one-way check valve 107 having an open end line 108. The check valve 107 blocks fluid egress from within the cassette, but a hydrophobic filter or other device may be used for this purpose instead. A short length of fluid vent line 109 from the first Tee 75 couples to the fluid input port 102.

Referring now specifically to FIGS. 5 and 6, it can be seen that the control valve 100 has a control valve housing 110 extending between the opposite broad faces of the cassette body and that the ports 102, 104 and 105 are at different levels, with the output port 105 being between the upper air input port (as seen in the figures) and the lower fluid input port 102. An internal valve stem 112 extends between the broad faces of the cassette, within the control valve housing, and is attached to a valve button 114 extending outside one face of the cassette 33. Thus the valve stem 112 may be shifted from the position shown to a depressed position relative to the control valve housing 112. In the position shown, a set of three spaced apart valve disks 116, 118 and 120, each having a peripheral O-ring 123, form two separate flow control chambers within the housing 110. When the valve stem 112 is in the position shown, the lower flow control chamber between the second and third disks 116, 118, respectively, provides communication between the fluid input port 102 and the output port 105. When the button 114 is depressed, however, flow is between the air input port 104 and the output port 105. The O-rings 123 in the disks insure against the intrusion of ambient air and the external leakage of fluid.

Thus, all that need be done to select whether air venting or fluid venting is preferred is to depress the valve stem 12 by the externally accessible button 114. The limit of depression of the valve stem 112 is defined by a stop surface 125 on the interior wall of the cassette 33. To ensure against shifting of the valve stem, once depressed, a depending spring latch 127 at the bottom of the valve stem 112 engages a projection 129 on the stop 125. A positive action release element (not shown) may be incorporated in the wall of the cassette adjacent the stop to permit reuse of the cassette, if desired. A wall opening may alternatively be incorporated in the cassette through which the spring latch 127 may be detached from the projection 129.

For purposes of reuse as well, the hydrophobic filter 62 is engaged into a Luer fitting 132 incorporated in the shunt tubing 96. The side opening 60 in the cassette (FIGS. 1 and 2) is made large enough, at least on one side of the cassette, to enable disengagement of the filter 62 from the Luer fitting 132.

This arrangement, therefore, offers capability both for resterilization, with removal, and then later replacement with a new spotted hydrophobic filter, and also enables the user or the fabricator to select air venting or fluid venting for surgical procedures.

It will be recognized by those skilled in the art that the control valve can be of different configurations than shown. It can use a valve slider with interior bores shaped to open vent air or liquid to the suction line dependent on axial position. Alternatively, the control valve can be arranged to switch paths by rotation of the valve element or by utilizing a different alternate position scheme.

Figure 7:
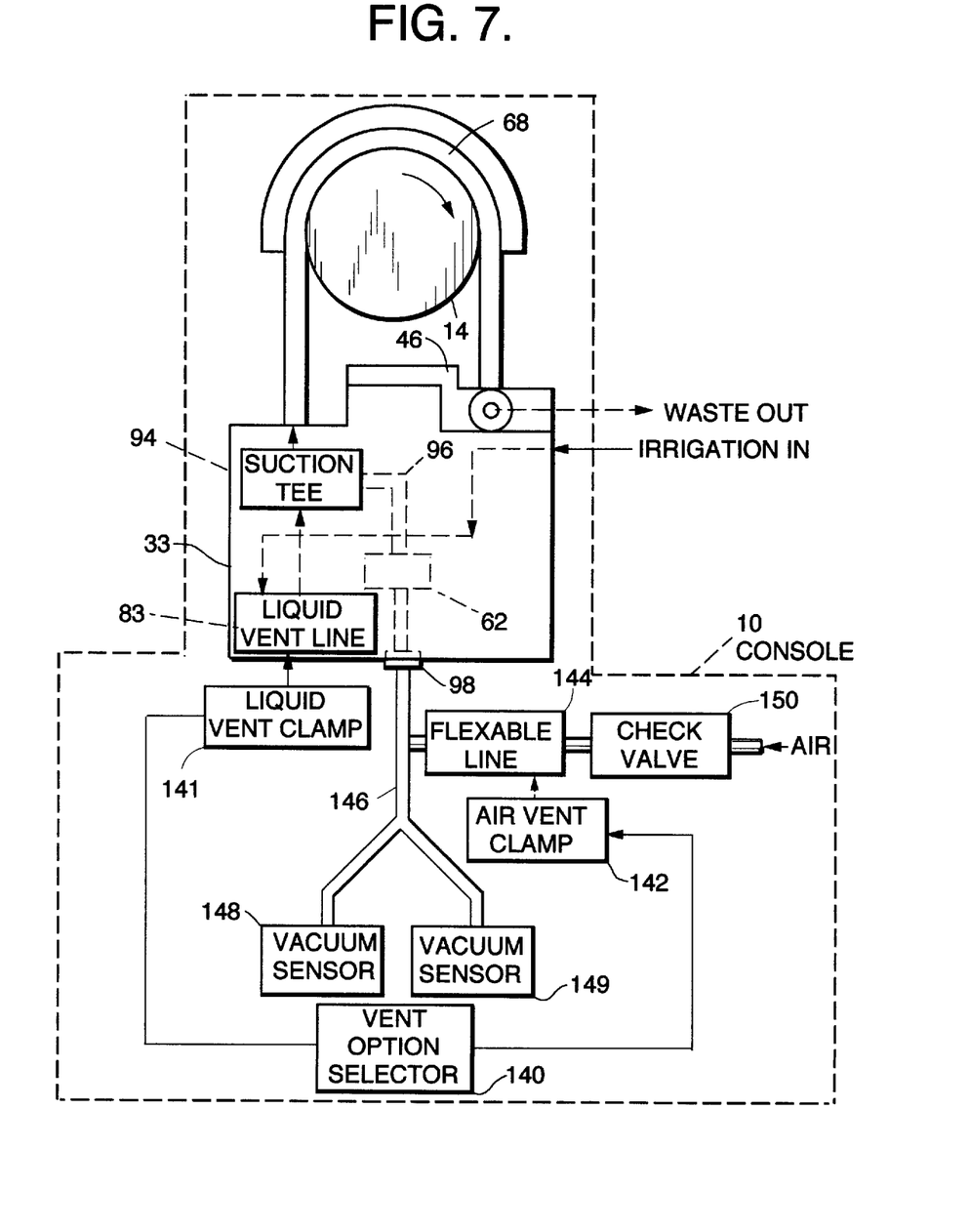
FIG. 7 is a block diagram representation of an alternative venting feature incorporated in a control system and usable in accordance with the invention.

While alternate venting control at the cassette is preferred, it can also be accomplished by using a control at the system console 16, as shown in FIG. 7.

For this purpose, referring now to FIG. 7, the console 16 includes a vent option selector 140, which can be a switch, for permitting actuation either of a liquid vent clamp or actuator 141 for engaging the liquid vent line 83, as shown in more detail in FIG. 3, or an air vent clamp or actuator 142 for engaging an air vent line 144. The flexible air vent line 144 couples into the interior line 146 within the console 10 that branches into the separate vacuum sensors 148, 149 that are employed within the console 16. A check valve 150 open to an air inlet and feeding the air vent line 144 can be employed in series with the air vent line 144 to prevent exterior leakage of any fluid that may pass the spotted hydrophobic filter 62 in the cassette 33.

By adding this capability to the console 10, the surgeon or other operator can make a selection of the type of venting to be used, even though the cassette assembly 25 remains unchanged. When liquid venting is to be used, the liquid vent clamp 141 is made actuable by the vent option selector 140, so that the clamp, normally pinching the liquid vent line 83 closed, can be opened to relieve suction at the suction Tee 94 in the previously described fashion. When the air vent clamp 142 is chosen, however, the liquid vent clamp 141 does not open the liquid vent line 83. Instead, the air vent clamp 142, normally closing the air vent line 144, permits that line 144 to open, allowing air through the check valve 150 and the air vent line 144 to reach the suction or third Tee 94, via the line 96 immediately relieving suction. This portion of the console 10 interior remains as sterile as when operated without the alternating venting feature.

Although a number of alternatives and modifications have been suggested, the invention is not limited thereto but includes all forms and variations within the scope of the appended claims.

We claim:

1. For use in a pumping control system for ophthalmic surgery having clamp actuator controls and an intermediate vent port in an interface slot below a mount face at the upper region of which a peristaltic pump is to engage a loop of tubing from a cassette installed in the mount face, a cassette device comprising:

an adapter element having a plate surface engageable against the mount face between the pump and interface slot, and including a shoulder extending proximally from the plate surface and offset to one side of the pump, the shoulder including a receiving opening adjacent one side of the mount face; and a cassette including a lower wall engageable in the interface slot, a distal wall engageable against the plate surface, and an upper wall engageable against the shoulder, the cassette further including flexible tubing accessible to the clamp actuator controls through the lower wall, an upper shoulder offset to the opposite side of the pump from the shoulder of the adapter element, and a flexible tubing length extending from the upper shoulder to the receiving opening of the adapter element, to wrap about the peristaltic pump.

2. A cassette device as set forth in claim 1 above, wherein the device includes an internal fluid vent path controllable by one of the clamp actuator controls, and further includes an alternate air vent path and selectable valve means coupled to both the fluid vent path and the air vent path before the clamp actuator control such that either vent path can be used as input.

3. A cassette device as set forth in claim 2 above, wherein the selectable valve means includes a position selecting element controllable exterior to the cassette, and the air vent path further includes an element blocking fluid egress.

4. A cassette device as set forth in claim 1 above, wherein the receiving opening comprises a retainer element including one opening having the flexible tubing length includes a coupler fitting within the retainer element.

5. A cassette device as set forth in claim 4 above, including in addition a waste collection bag mountable proximate to the cassette and a length of flexible tubing coupled to the coupler and insertable into the bag, and wherein the retainer element includes an opening defining a side slot and the coupler comprises a cylindrical element slidably fitting within the side slot.

6. A cassette device as set forth in claim 1 above, wherein the pumping control system has a suction level measuring system for coupling at the interface slot via a vent port to a vent fitting on the cassette, wherein the cassette includes a vent fitting engaging the vent port, and a spotted hydrophobic filter in the vent flow path, and wherein the cassette further includes means for replacing the spotted hydrophobic filter after use such that the cassette may be optionally resterilized and reused.

7. In a cassette for providing an irrigation flow to a handpiece and receiving an aspiration flow under a suction from the handpiece, wherein the cassette includes an occludable shunt coupling between the suction source and the irrigation flow, to provide a fluid flow to relieve suction, an arrangement for providing alternative usage of fluid flow or air flow to the aspiration flow comprising:

an air vent conduit system disposed to receive air; and a selectable position valve device having an positionable valve element movable between air selection and fluid selection positions, the valve element being coupled to receive irrigation fluid flow, and air flow at different input positions, and coupled to the occludable aspiration line at a third output position, the valve element including sealing elements disposed to block unwanted fluid flow between positions, while coupling the fluid input to the output in a first position, and coupling the air input to the output in the second position.

8. An arrangement as set forth in claim 7 above, wherein the air vent line includes an element for blocking fluid egress, and wherein the selectable valve device comprises a valve cylinder, a valve stem and a group of spaced apart disks along the valve stem, each including an encircling O-ring in contact with the cylinder wall and wherein the output is disposed between the air inlet and the fluid inlet.

9. An arrangement as set forth in claim 8 above, wherein the valve element includes a central cylindrical shaft, and an upper manually actuable button end, and wherein the lower end of the valve element includes a stop for engaging the valve element at a lower limit axial position.

10. A tubing configuration for a cassette for ophthalmic surgery applications, the cassette being of the type having a housing, an edge wall on the housing along a first side and a pump loop extending from an edge wall on a second side, the edge wall on the first side including a pair of spaced apart actuator access apertures and an intermediate vent aperture, and the cassette further including internal bosses adjacent the actuator access apertures and flexible tubing wrapped around the bosses to be clamped against the bosses by external actuators; the cassette further including an irrigation input line, an aspiration line and a waste line from the pump loop, the cassette further including flexible vent tubing coupled to receive irrigation input and wrapped around a first of the bosses before coupling to the pump loop to enable irrigation fluid to be supplied to the pump loop for breaking suction upon command, comprising:

an air vent input line;

a selectable position valve element coupled to the air input line and coupled to the irrigation input flow at a different position, the selectable position valve also being coupled to the vent tubing at a third position, the valve being operable to couple either the air input line or the irrigation input line to the first occludable line, by change of position.

11. A system for controlling relief of suction in a cassette having a conduit subjected to a suction force, comprising the combination of:
- a venting connection coupled to the suction line;
- a first vent line coupled to the venting connection and open to air;
- a second vent line coupled to the venting connection and open to fluid; and
- control means normally maintaining the vent lines closed and selectably allowing one of the vent lines to open.

12. The invention as set forth in claim 11 above, wherein the first vent line and the second vent line are both disposed in the cassette, and wherein the control means includes controllable valve means for selecting which line is to be coupled to the venting connection.

13. A device as set forth in claim 11 above, wherein the cassette includes a suction level sensing line connectable to the console, and coupled to the venting connection, and a liquid vent line within the cassette positioned to be externally controlled;
- wherein the console includes an actuable control for engaging the controllable vent line in the cassette and a second actuable control for air venting, and wherein the console further includes an air vent line coupled to the suction level sensing line in the cassette and controllable by the second control; and
- a selection control at the console and coupled to enable operation of either of the two actuable controls in the console.

* * * * *